United States Patent [19]
Brandes et al.

[11] Patent Number: 6,063,788
[45] Date of Patent: *May 16, 2000

[54] BICYCLIC-FUSED PYRIDINES

[75] Inventors: Arndt Brandes; Michael Lögers; Gunter Schmidt, all of Wuppertal; Rolf Angerbauer, Kobe; Carsten Schmeck, Wuppertal; Klaus-Dieter Bremm, Recklinghausen; Hilmar Bischoff, Wuppertal; Delf Schmidt, Wuppertal; Joachim Schuhmacher, Wuppertal, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/883,067

[22] Filed: Jun. 27, 1997

[30] Foreign Application Priority Data

Jul. 8, 1996 [DE] Germany .................... 196 27 430

[51] Int. Cl.⁷ .................... A61K 31/44; C07D 221/16
[52] U.S. Cl. .................... 514/290; 546/111
[58] Field of Search .................... 546/111; 514/290

[56] References Cited

U.S. PATENT DOCUMENTS

| 4,814,346 | 3/1989 | Albert et al. . |
| 5,006,530 | 4/1991 | Angerbauer et al. . |
| 5,169,857 | 12/1992 | Angerbauer et al. . |
| 5,254,565 | 10/1993 | Meguro et al. . |

FOREIGN PATENT DOCUMENTS

| 444533 | 9/1991 | European Pat. Off. . |
| 481243 | 4/1992 | European Pat. Off. . |

OTHER PUBLICATIONS

Petrow, et al.: "New Synthesis of Heterocyclic compounds, Part X, Azafluorenones" Journal of the Chemical Society, 1949, pp. 2134–2137, XP002049743.

Dinchuck, Hart, Gonzales, Karmann, Schmidt, Wirak, BBA (1995) vol. 1295, p. 301.

*Primary Examiner*—Patricia L. Morris
*Attorney, Agent, or Firm*—Norris, McLaughlin & Marcus, P.A.

[57] ABSTRACT

Bicyclic-fused pyridines are prepared by introducing the appropriate side chain by reaction of the corresponding aldehydes with the aid of Wittig or Grignard reagents. The bicyclic-fused pyridines are suitable as active compounds in medicaments, in particular in medicaments for the treatment of arteriosclerosi.

3 Claims, No Drawings

BICYCLIC-FUSED PYRIDINES

The present invention relates to bicyclic-fused pyridines, processes for their preparation and their use in medicaments.

The publication U.S. Pat. No. 5,169,857 A2 discloses 7-(polysubstituted pyridyl)-6-heptenoates for the treatment of arteriosclerosis, lipoproteinaemia and hyperlipoproteinaemia. The preparation of 7-(4-aryl-3-pyridyl)-3,5-dihydroxy-6-heptenoates is additionally described in the publication EP 325 130 A2. The compound 3-benzoyl-2-methyl-4-phenyl-indeno[1,2-b]pyridin-5-one is furthermore disclosed in the publication J. Chem. Soc. 1949, 2134, 2137.

The present invention relates to bicyclic-fused pyridines of the general formula (I)

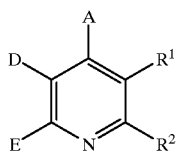

(I)

A represents aryl having 6 to 10 carbon atoms, which is optionally substituted up to 5 times in an identical or different manner by halogen, hydroxyl, trifluoromethyl, trifluoromethoxy, nitro or by straight-chain or branched alkyl, acyl, hydroxyalkyl or alkoxy each having up to 7 carbon atoms, or by a group of the formula —NR³R⁴,
in which
$R^3$ and $R^4$ are identical or different and denote hydrogen, phenyl or straight-chain or branched alkyl having up to 6 carbon atoms, D represents a radical of the formula

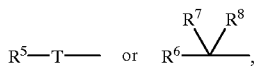

in which
$R^5$ and $R^6$ independently of one another denote cycloalkyl having 3 to 8 carbon atoms, or
aryl having 6 to 10 carbon atoms,
or a 5- to 7-membered aromatic, optionally benzo-fused heterocycle having up to 3 heteroatoms from the series consisting of S, N and/or O, each of which is optionally substituted up to 5 times in an identical or different manner by trifluoromethyl, trifluoromethoxy, halogen, hydroxyl, carboxyl, by straight-chain or branched alkyl, acyl, alkoxy or alkoxycarbonyl each having up to 6 carbon atoms or by phenyl, phenoxy or thiophenyl, which for their part can be substituted by halogen, trifluoromethyl or trifluoromethoxy,
or the cycles are substituted by a group of the formula —NR⁹R¹⁰,
in which
$R^9$ and $R^{10}$ are identical or different and have the meaning of $R^3$ and $R^4$ indicated above, T denotes a straight-chain or branched alkylene or alkenylene chain each having up to 10 carbon atoms, each of which is optionally substituted up to 2 times by hydroxyl,
$R^7$ denotes hydrogen or halogen, and
$R^8$ denotes hydrogen, halogen, azido, trifluoromethyl, hydroxyl, tri fluoromethoxy, straight-chain or branched alkoxy having up to 5 carbon atoms or a radical of the formula —NR¹¹R¹²,
in which
$R^{11}$ and $R^{12}$ are identical or different and have the meaning of $R^3$ and $R^4$ indicated above, or
$R^7$ and $R^8$, together with the C atom, form a carbonyl group, E represents cycloalkyl having 3 to 8 carbon atoms, or represents straight-chain or branched alkyl having up to 8 carbon atoms, which is optionally substituted by cycloalkyl having 3 to 8 carbon atoms or by hydroxyl,
$R^1$ and $R^2$ together form a straight-chain or branched alkylene chain having up to 8 carbon atoms, to which a phenyl ring is fused and which must be substituted by a carbonyl group or a group of the formula

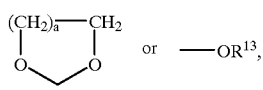

or —OR¹³, in which
a represents a number 1, 2 or 3, and
$R^{13}$ denotes hydrogen, straight-chain or branched alkyl, acyl or alkoxycarbonyl each having up to 6 carbon atoms or a radical of the formula —SiR¹⁴R¹⁵R⁶,
in which
$R^{14}$, $R^{15}$ and $R^{16}$ are identical or different and denote straight-chain or branched alkyl having up to 6 carbon atoms or phenyl,
and where both ring systems are optionally substituted up to 3 times in an identical or different manner by halogen, carboxyl or by straight-chain or branched alkyl, alkoxy or alkoxycarbonyl each having up to 6 carbon atoms, and their salts and their N-oxides, with the exception of the compound 3-benzoyl-2-methyl-4-phenyl-indeno[1,2-b]pyridin-5-one.

The bicyclic-substituted pyridines according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a known manner.

Heterocycle, if appropriate benzo-fused, in the context of the invention in general represents a saturated or unsaturated 5- to 7-membered, preferably 5- to 6-membered, heterocycle, which can contain up to 3 heteroatoms from the series consisting of S, N and/or O. Examples which may be mentioned are: indolyl, isoquinolyl, quinolyl, benzo[b] thiophenyl, benzo[b]furyl, pyridyl, thienyl, furyl, pyrrolyl, thiazolyl, oxazolyl, imidazolyl, morpholinyl or piperidyl. Quinolyl, furyl, pyridyl and thienyl are preferred.

Preferred compounds of the general formula (I) according to the invention are those
in which A represents naphthyl or phenyl, each of which is optionally substituted up to 3 times in an identical or different manner by fluorine, chlorine, bromine, hydroxyl, trifluoromethyl, trifluoromethoxy, nitro or by straight-chain or branched alkyl or alkoxy each having up to 6 carbon atoms, D represents a radical of the formula

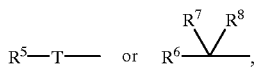

in which
R$^5$ and R$^6$ independently of one another denote cyclopropyl, cyclopentyl or cyclohexyl, or denote naphthyl, phenyl, pyridyl, quinolyl, indolyl, benzothiazolyl or tetrahydronaphthalenyl, each of which is optionally substituted up to 3 times in an identical or different manner by trifluoromethyl, trifluoromethoxy, fluorine, chlorine, bromine, hydroxyl, carboxyl, by straight-chain or branched alkyl, acyl, alkoxy or alkoxycarbonyl each having up to 5 carbon atoms or by phenyl, phenoxy or thiophenyl, which for their part can be substituted by fluorine, chlorine, bromine, trifluoromethyl or trifluoromethoxy, T denotes a straight-chain or branched alkylene or alkenylene chain each having up to 6 carbon atoms, each of which is optionally substituted up to 2 times by hydroxyl, R$^7$ denotes hydrogen, fluorine, chlorine or bromine, and R$^8$ denotes hydrogen, fluorine, chlorine, bromine, azido, trifluoromethyl, hydroxyl, trifluoromethoxy, straight-chain or branched alkoxy having up to 4 carbon atoms, or R$^7$ and R$^8$ form a carbonyl group with the C atom, E represents cyclopropyl, cyclobutyl, cyclopentyl, cyclohexyl or cycloheptyl, or represents straight-chain or branched alkyl having up to 6 carbon atoms, which is optionally substituted by cyclopropyl, cyclobutyl, cyclohexyl, cycloheptyl or by hydroxyl, R$^1$ and R$^2$ together form a straight-chain or branched alkylene chain having up to 6 carbon atoms, to which a phenyl ring is fused and which must be substituted by a carbonyl group or a group of the formula

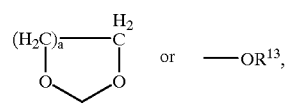

in which
a denotes a number 1, 2 or 3 and
R$^{13}$ denotes hydrogen, straight-chain or branched alkyl, acyl or alkoxycarbonyl each having up to 5 carbon atoms or a radical of the formula —SiR$^{14}$R$^{15}$R$^{16}$,
in which
R$^{14}$, R$^{15}$ and R$^{16}$ are identical or different and denote straight-chain or branched alkyl having up to 5 carbon atoms or phenyl,
and where both ring systems are optionally substituted up to 3 times in an identical or different manner by fluorine, chlorine, bromine, or by straight-chain or branched alkyl, alkoxy or alkoxycarbonyl each having up to 5 carbon atoms, and their salts and their N-oxides, with the exception of the compound 3-benzoyl-2-methyl-4-phenyl-indeno[1,2-b] pyridin-5-one.

Particularly preferred compounds of the formula (I) are those
in which

A represents phenyl which is optionally substituted by fluorine, chlorine, methyl, methoxy, nitro or trifluoromethyl, D represents a radical of the formula

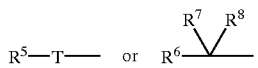

in which
R$^5$ and R$^6$ independently of one another denote cyclopropyl, phenyl, pyridyl, quinolyl, indolyl, benzothiazolyl or tetrahydronaphthalenyl, each of which is optionally substituted up to 2 times in an identical or different manner by trifluoromethyl, nitro, trifluoromethoxy, fluorine, chlorine, bromine, hydroxyl, carboxyl, by straight-chain or branched alkyl, acyl, alkoxy or alkoxycarbonyl each having up to 4 carbon atoms or by phenyl, phenoxy or thiophenyl, which for their part can be substituted by fluorine, chlorine, bromine, trifluoromethyl or trifluoromethoxy, T denotes a straight-chain or branched alkylene or alkenylene chain each having up to 4 carbon atoms, each of which is optionally substituted up to 2 times by hydroxyl, R$^7$ denotes hydrogen or fluorine, and R$^8$ denotes hydrogen, fluorine, chlorine, bromine, azido, trifluoromethyl, hydroxyl, trifluoromethoxy or methoxy, or R$^7$ and R$^8$, together with the C atom, form a carbonyl group, E represents cyclopropyl, cyclobutyl, cyclopentyl, cyclohexyl or cycloheptyl, or represents straight-chain or branched alkyl having up to 5 carbon atoms, which is optionally substituted by cyclopentyl or cyclohexyl, R$^1$ and R$^2$ together form a straight-chain or branched alkylene chain having up to 5 carbon atoms, to which a phenyl ring is fused and which must be substituted by a carbonyl group or a group of the formula

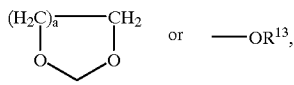 or —OR$^{13}$, in which a denotes a number 1, 2 or 3 and

R$^{13}$ denotes hydrogen, straight-chain or branched alkyl, acyl or alkoxycarbonyl each having up to 4 carbon atoms or a radical of the formula —SiR$^{14}$R$^{15}$R$^{16}$, in which R$^{14}$, R$^{15}$ and R$^{16}$ are identical or different and denote straight-chain or branched alkyl having up to 4 carbon atoms or phenyl, and where both ring systems are optionally substituted up to 3 times in an identical or different manner by fluorine, chlorine, straight-chain or branched alkyl, alkoxy or alkoxycarbonyl each having up to 4 carbon atoms, and their salts and N-oxides, with the exception of the compound 3-benzoyl-2-methyl-4-phenyl-indeno[1,2-b]pyridin-5-one.

Very particularly preferred compounds of the general formula (I) according to the invention are those in which A represents phenyl which is optionally substituted by fluorine or chlorine, E represents isopropyl or cyclopentyl.

A process for the preparation of the compounds of the general formula (I) according to the invention has additionally been found, characterized in that in compounds of the general formula (II)

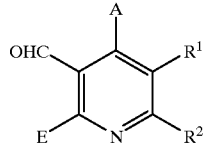

(II)

in which

A, E, R$^1$ and R$^2$ have the meaning indicated above, first, with organometallic reagents, the substituent D is introduced in inert solvents according to a Grignard or Wittig reaction, and if appropriate the substituents mentioned under A, E and/or R$^1$ and R$^2$ are varied or introduced according to customary methods.

The process according to the invention can be illustrated by way of example by the following reaction scheme:

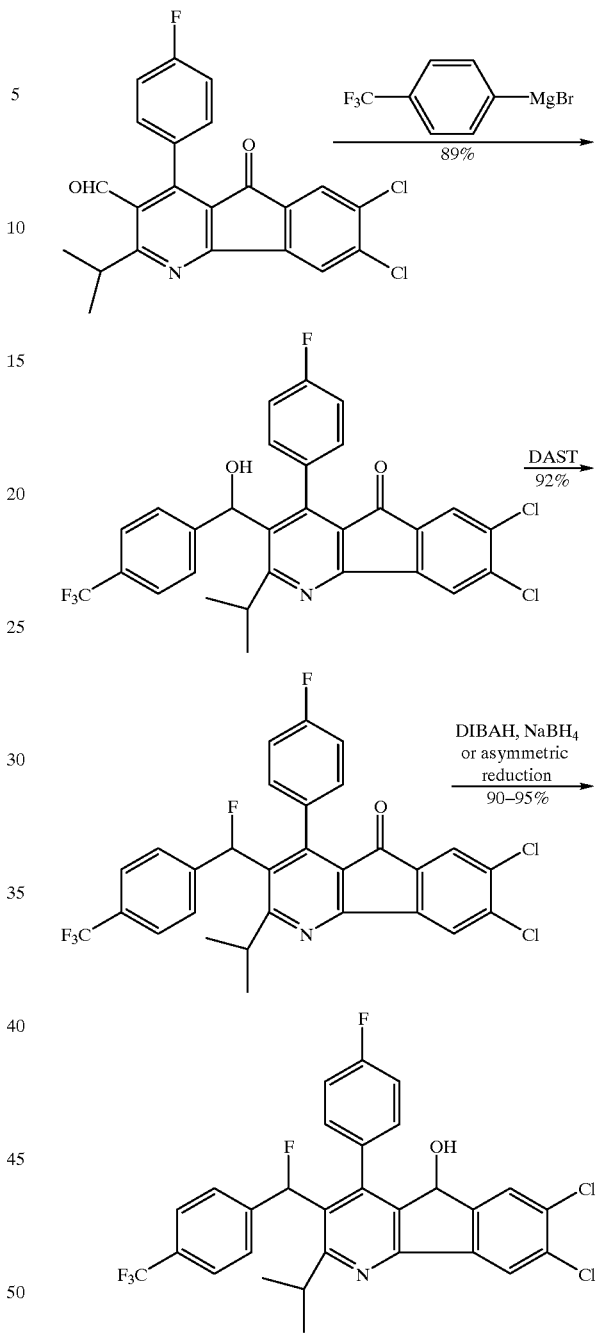

Suitable solvents are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

Possible bases for the individual steps are the customary strongly basic compounds. These preferably include organolithium compounds such as, for example, n-butyllithium, sec-butyllithium, tert-butyllithium or phenyllithium, or amides such as, for example, lithium diisopropylamide, sodium amide or potassium amide, or lithium hexamethylsilylamide, or alkali metal hydrides such as sodium hydride or potassium hydride. n-Butyllithium or sodium hydride is particularly preferably employed.

Suitable organometallic reagents are, for example, systems such as Mg/bromobenzotrifluoride and p-trifluoromethylphenyllithium.

Suitable Wittig reagents are the customary reagents. 3-Tri-fluoromethylbenzyltriphenylphosphonium bromide is preferred.

In general, suitable bases are one of the abovementioned bases, preferably Li bis-(triethylbutyl)amide.

The base is employed in an amount from 0.1 mol to 5 mol, preferably from 0.5 mol to 2 mol, in each case relative to 1 mol of the starting compound.

The reaction with Wittig reagents is in general carried out in a temperature range from 0° C. to 150° C., preferably at 25° C. to 40° C.

The Wittig reactions are in general carried out at normal pressure. However, it is also possible to carry out the process at reduced pressure or at elevated pressure (e.g. in the range from 0.5 to 5 bar).

The reductions are in general carried out using reducing agents, preferably using those which are suitable for the reduction of ketones to hydroxyl compounds. Particularly suitable in this context is reduction with metal hydrides or complex metal hydrides in inert solvents, if appropriate in the presence of a trialkylborane. The reduction is preferably carried out using complex metal hydrides such as, for example, lithium borohydride, sodium borohydride, potassium borohydride, zinc borohydride, lithium trialkylborohydride, diisobutylaluminium hydride or lithium aluminium hydride. Reduction using diisobutylaluminium hydride and sodium borohydride is very particularly preferred.

The reducing agent is in general employed in an amount from 1 mol to 10 mol, preferably from 1 mol to 3 mol, relative to 1 mol of the compounds to be reduced.

The reduction in general proceeds in a temperature range from −78° C. to +50° C., preferably from −78° C. to 0° C., particularly preferably at −78° C., in the case of diisobutylaluminium hydride in each case depending on the choice of the reducing agent and solvent.

The reduction in general proceeds at normal pressure, but it is also possible to work at elevated or reduced pressure.

Derivatizations which may be mentioned by way of example are the following types of reaction:
  oxidations, reductions, hydrogenations, halogenation, Wittig/Grignard reactions and amidations/sulphoamidations.

Possible bases for the individual steps are the customary strongly basic compounds. These preferably include organolithium compounds such as, for example, n-butyllithium, sec-butyllithium, tert-butyllithium or phenyllithium, or amides such as, for example, lithium diisopropylamide, sodium amide or potassium amide, or lithium hexamethylsilylamide, or alkali metal hydrides such as sodium hydride or potassium hydride. n-Butyllithium or sodium hydride is particularly preferably employed.

Suitable bases are additionally the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen carbonate. Sodium hydroxide or potassium hydroxide is particularly preferably employed.

Suitable solvents for the individual reaction steps are also alcohols such as methanol, ethanol, propanol, butanol or tert-butanol. tert-Butanol is preferred.

It may be necessary to carry out some reaction steps under a protective gas atmosphere.

The halogenations are in general carried out in one of the abovementioned chlorinated hydrocarbons or toluene, methylene chloride and toluene being preferred.

Suitable halogenating agents are, for example, diethylaminosulphur trifluoride (DAST) or SOCl$_2$.

The halogenation in general proceeds in a temperature range from −78° C. to +50° C., preferably from −78° C. to 0° C., particularly preferably at −78° C., in each case depending on the choice of the halogenating agent and solvent.

The halogenation in general proceeds at normal pressure, but it is also possible to work at elevated or reduced pressure.

The compounds of the general formula (II) are new and can be prepared by a process in which
by reaction of the compounds of the general formula (III)

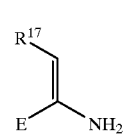

(III)

in which
  E has the meaning indicated above and
  $R^{17}$ represents $C_1$–$C_4$-alkoxycarbonyl,
with aldehydes of the general formula (IV)

A—CHO    (IV)

in which
  A has the meaning indicated above
and compounds of the general formula (V)

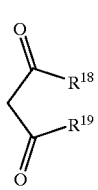

(V)

in which
  $R^{18}$ and $R^{19}$, including a carbonyl group, encompass the scope of meaning of $R^1$ and $R^2$ indicated above,
the compounds of the general formula (VI)

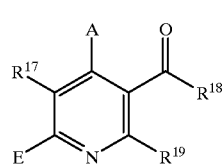

(VI)

in which
  A, E, $R^{17}$, $R^{18}$ and $R^{19}$ have the meaning indicated above,
  are prepared,
and in a last step the alkoxycarbonyl group ($R^{17}$) is converted into an aldehyde group by a reduction/oxidation sequence.

Suitable solvents for the oxidation are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Methylene chloride is preferred.

Suitable oxidizing agents are, for example, sulphur trioxide-pyridine complex, cerium(IV) ammonium nitrate, 2,3-dichloro-5,6-dicyano-benzoquinone, pyridinium chlorochromate (PCC), osmium tetroxide and manganese dioxide. Sulphur trioxide-pyridine complex is preferred.

The oxidizing agent is employed in an amount from 1 mol to 10 mol, preferably from 2 mol to 5 mol, relative to 1 mol of the compounds of the general formula (IV).

The oxidation in general proceeds in a temperature range from $-50°$ C. to $+100°$ C., preferably from $0°$ C. to room temperature.

The oxidation in general proceeds at normal pressure. However, it is also possible to carry out the oxidation at elevated or reduced pressure.

The compounds of the general formula (III), (IV) and (V) are known per se or can be prepared by customary methods.

The compounds of the general formula (VI) are new and can be prepared as described above.

The compounds of the general formula (I) according to the invention have an unforeseeable spectrum of pharmacological action.

The compounds of the general formula (I) according to the invention have useful pharmacological properties which are superior in comparison with the prior art, in particular they are highly effective inhibitors of cholesterol ester transfer protein (CETP) and stimulate reverse cholesterol transport. Reactive compounds according to the invention cause a lowering of the LDL cholesterol level in the blood with simultaneous raising of the HDL cholesterol level. They can therefore be employed primary and for the treatment of hyperlipoproteinaemia, hypolipoproteinaemia, dislipidaemia, hypertriglyceridaemia, combined hyperlipidaemia or arteriosclerosis.

The pharmacological actions of the substances according to the invention were determined in the following test:

CETP Inhibition Testing

Obtainment of CETP

CETP is obtained from human plasma in partially purified form by differential centrifugation and column chromatography and used for the test. To this end, human plasma is adjusted to a density of 1.21 g per ml using NaBr and centrifuged at $4°$ C. for 18 h at 50,000 rpm. The bottom fraction (d>1.21 g/ml) is applied to a Sephadex®phenyl-sepharose 4B (Pharmacia) column, washed with 0.15 M NaCl/0.001 M trisHCl pH 7.4 and then eluted with distilled water. The CETP-active fractions are pooled, dialysed against 50 mM Na acetate pH 4.5 and applied to a CM-Sepharose® (Pharmacia) column. The column is then eluted using a linear gradient (0–1 M NaCl). The pooled CETP fractions are dialysed against 10 mM tris HCl pH 7.4 and then further purified by chromatography on a Mono Q® column (Pharmacia).

Obtainment of radiolabelled HDL 50 ml of fresh human EDTA plasma are adjusted to a density of 1.12 using NaBr and centrifuged at 50,000 rpm for 18 h at $4°$ C. in a Ty 65 rotor. The upper phase is used to obtain cold LDL. The lower phase is dialysed against 3×4 l of PDB buffer (10 mM tris/HCl pH 7.4, 0.15 mM NaCl, 1 mM EDTA, 0.02% $NaN_3$). 20 $\mu$l of $^3$H-cholesterol (Dupont NET-725; 1 $\mu C/\mu l$ dissolved in ethanol!) are then added per 10 ml of retentate volume and the mixture is incubated under $N_2$ at $37°$ C. for 72 h.

The mixture is then adjusted to the density 1.21 using NaBr and centrifuged at $20°$ C. for 18 h at 50,000 rpm in the Ty 65 rotor. The upper phase is recovered and the lipoprotein fractions are purified by gradient centrifugation. To this end, the isolated, labelled lipoprotein fraction is adjusted to a density of 1.26 using NaBr. Each 4 ml of this solution are covered with a layer of 4 ml of a solution of density 1.21 and 4.5 ml of a solution of 1.063 (density solutions from PDB buffer and NaBr) in centrifuge tubes (SW 40 rotor) and then centrifuged in the SW 40 rotor for 24 h at 38,000 rpm and $20°$ C. The intermediate layer lying between the densities 1.063 and 1.21 and containing the labelled HDL is dialysed at $4°$ C. against 3×100 volumes of PDB buffer.

The retentate contains radiolabelled $^3$H-CE-HDL, which is used for the test, adjusted to about $5×10^6$ cpm per ml.

CETP Test

To test the CETP activity, the transfer of $^3$H-cholesterol ester from human HD lipoproteins to biotinylated LD lipoproteins is measured.

The reaction is ended by addition of streptavidin-SPA®beads (Amersham) and the transferred radioactivity is determined directly in a liquid scintillation counter.

In the test mixture, 10 $\mu$l of HDL-$^3$H-cholesterol ester (~50,000 cpm) are incubated at $37°$ C. for 18 h with 10 $\mu$l of biotin-LDL (Amersham) in 50 mM Hepes/0.15 M NaCl/ 0.1% bovine serum albumin/0.05% $NaN_3$ pH 7.4 with 10 $\mu$l of CETP (1 mg/ml) and 3 $\mu$l of solution of the substance to be tested (dissolved in 10% DMSO/1% RSA). 200 $\mu$l of the SPA-streptavidin bead solution (TRKQ 7005) are then added, the mixture is incubated further for 1 h with shaking and then measured in the scintillation counter. As controls, corresponding incubations with 10 $\mu$l of buffer, 10 $\mu$l of CETP at $4°$ C. and 10 $\mu$l of CETP at $37°$ C. are used.

The activity transferred into the control mixtures with CETP at $37°$ C. is rated as 100% transfer. The substance concentration at which this transfer is reduced by half is indicated as the $IC_{50}$ value.

In Table A which follows, the $IC_{50}$ values (mol/l) are indicated for CETP inhibitors:

TABLE A

| Example No. | $IC_{50}$ value (mol/l) |
| --- | --- |
| 14 | $6 \times 10^{-8}$ |
| 22 | $2.4 \times 10^{-7}$ |
| 27 | $3 \times 10^{-7}$ |

Ex Vivo Activity of the Compounds According to the Invention

Syrian golden hamsters from in-house breeding are anaesthetized after fasting for 24 hours (0.8 mg/kg of atropine, 0.8 mg/kg of Ketavet® s.c., 30' later 50 mg/kg of Nembutal i.p.). The jugular vein is then exposed and cannulated. The test substance is dissolved in a suitable solvent (as a rule Adalat placebo solution: 60 g of glycerol, 100 ml of $H_2O$, PEG-400 to 1000 ml) and administered to the animals via a PE catheter inserted in the jugular vein. The control animals receive the same volume of solvent without test substance. The vein is then tied off and the wound is closed. The administration of the test substances can also be carried out p.o., by orally administering the substances dissolved in DMSO and suspended in 0.5% Tylose by means of a stomach tube. The control animals receive identical volumes of solvent without test substance.

After various times—up to 24 hours after administration—blood (about 250 µl) is taken from the animals by puncture of the retro-orbital venous plexus. Clotting is ended by incubation at 4° C. overnight, then centrifugation is carried out at 6000×g for 10 minutes. In the serum thus obtained, CETP activity is determined by the modified CETP test. As for the CETP test described above, the transfer of $^3$H-cholesterol ester from HD lipoproteins to biotinylated LD lipoproteins is measured.

The reaction is ended by addition of Streptavidin-SPA® beads (Amersham) and the transferred radioactivity is determined directly in the liquid scintillation counter.

The test mixture is carried out as described under "CETP test". For the testing of the serum, only 10 µl of CETP are replaced by 10 µl of the corresponding serum samples. As controls, corresponding incubations with sera of untreated animals are used.

The activity transferred in the control mixtures with control sera is rated as 100% transfer. The substance concentration at which this transfer is reduced to a half is indicated as the $ED_{50}$ value.

TABLE B $ED_{50}$ values for ex vivo activity

| Ex. | $ED_{50}$ | % Inhibition at 10 mg/kg |
|---|---|---|
| 14 | <10 mg/kg | 64.0% |
| 19 | >10 mg/kg | 46.0% |
| 29 | >10 mg/kg | 17.2% |

In Vivo Activity of the Compounds According to the Invention

In experiments to determine the oral action on lipoproteins and triglycerides, test substance dissolved in DMSO and 0.5% Tylose suspended by means of a stomach tube are administered orally to Syrian golden hamsters from in-house breeding. To determine the CETP activity, blood (about 250 µl) is taken by retro-orbital puncture before the start of the experiment. The test substances are then administered orally by means of a stomach tube. The control animals receive identical volumes of solvents without test substance. The feed is then withdrawn from the animals and blood is taken at various times—up to 24 hours after substance administration—by puncture of the retro-orbital venous plexus.

Clotting is ended by incubation at 4° C. overnight, then centrifugation at 6000×g is carried out for 10 minutes. In the serum thus obtained, the content of cholesterol and triglycerides is determined with the aid of modified commercially available enzyme tests (cholesterol enzymatic 14366 Merck, triglycerides 14364 Merck). Serum is suitably diluted using physiological saline solution.

100 µl of serum dilution are mixed with 100 µl of test substance in 96-hole plates and incubated at room temperature for 10 minutes. The optical density is then determined at a wavelength of 492 nm using an automatic plate-reading apparatus. The triglyceride or cholesterol concentration contained in the samples is determined with the aid of a standard curve measured in parallel.

The determination of the content of HDL cholesterol is carried out according to the manufacturer's instructions after precipitation of the ApoB-containing lipoproteins by means of a reagent mixture (Sigma 352-4 HDL cholesterol reagent).

TABLE C

HDL rise in in vivo experiments

| Ex. | Dose (mg/kg) | % HDL rise |
|---|---|---|
| 18 | 2 × 10 | 3.3 |
| 19 | 2 × 10 | 17.1 |
| 20 | 2 × 10 | 11.14 |

In Vivo Activity in Transgenic hCETP Mice

Transgenic mice from in-house breeding (Dinchuck, Hart, Gonzalez, Karmann, Schmidt, Wirak; BBA (1995), 1295, 301) were administered the substances to be tested in the feed. Before the start of the experiment, blood was taken retro-orbitally from the mice in order to determine cholesterol and triglycerides in the serum. The serum was obtained as described above for hamsters by incubation at 4° C. overnight and subsequent centrifugation at 6000×g. After one week, blood was again taken from the mice in order to determine lipoproteins and triglycerides. The change in the parameters measured is expressed as a percentage change compared with the starting value.

TABLE D

| Ex. | HDL | LDL | Triglyceride |
|---|---|---|---|
| 14 (100 ppm) | 22.0% | −10.5% | −9.7% |

The invention additionally relates to the combination of bicyclic-fused pyridines of the general formula (I) with a glucosidase and/or amylase inhibitor for the treatment of familial hyperlipidaemias, of obesity (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formula (I) according to the invention is preferred.

The compounds according to the invention can furthermore be used in combination with cholesterol-lowering vastatins or ApoB-lowering principles in order to treat dyslipidaemias, combined hyperlipidaemias, hypercholesterolaemias or hypertriglyceridaemias.

The combinations mentioned can also be employed for the primary or secondary prevention of coronary heart disease.

Vastatins in the context of the invention are, for example, lovastatin, simvastatin, pravastatin, fluvastatin, atorvastatin and cerivastatin. ApoB-lowering agents are, for example, MTP inhibitors.

The combination of cerivastatin or ApoB inhibitors with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of approximately 0.5 to 90% by weight of the total mixture, i.e. in amounts which are adequate in order to achieve the dosage range indicated.

The formulations are prepared, for example, by extending the active compounds with solvents and/or excipients, if appropriate using emulsifiers and/or dispersants, it being possible, for example, when water is used as a diluent, optionally to use organic solvents as auxiliary solvents.

Administration takes place in the customary manner, intravenously, parenterally, perlingually or orally, preferably orally.

In the case of parenteral administration, solutions of the active compound can be employed using suitable liquid excipient materials.

In general, it has proved advantageous in the case of intravenous administration to administer amounts of approximately 0.001 to 1 mg/kg, preferably of approximately 0.01 to 0.5 mg/kg of body weight to achieve effective results, and in the case of oral administration the dose is approximately 0.01 to 20 mg/kg, preferably 0.1 to 10 mg/kg of body weight.

In spite of this, if appropriate it may be necessary to deviate from the amounts mentioned, mainly depending on the body weight or the type of administration route, on individual behaviour towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into several individual doses over the course of the day.

Abbreviations Used
C=cyclohexane
EA=ethyl acetate
PE=petroleum ether
THF=tetrahydrofuran

STARTING COMPOUNDS

EXAMPLE I

Methyl 7,8-dichloro-4-(4-fluoro-phenyl)-2-isopropyl-5-oxo-5H-indeno[1,2-b]pyridine-3-carboxylate

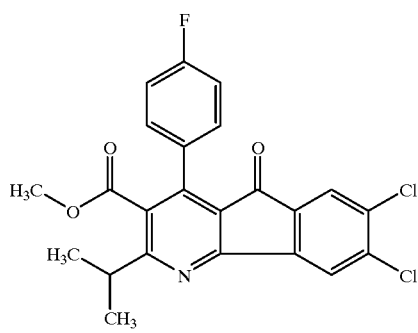

44 g of 5,6-dichloro-1,3-indanedione (204 mmol), 29.2 g of methyl 3-amino-4-methyl-2-pentenoate (204 mmol) and 25.3 g of p-fluorobenzaldehyde (204 mmol) are dissolved in 300 ml of toluene and the mixture is heated to reflux temperature in a water separator for 18 h. After cooling, it is filtered and the filtrate is concentrated. The crude product is eluted on 1.2 kg of silica gel (0.04–0.063 mm) using cyclohexane: ethyl acetate 9:1.

Yield: 14.5 g (16% of theory)
$R_f$=0.37 (C/EA 9:1)

EXAMPLE II 7,8-Dichloro-4-(4-fluorophenyl)-3-hydroxymethyl-2-isopropyl-5H-indeno[1,2-b]pyridin-5-ol

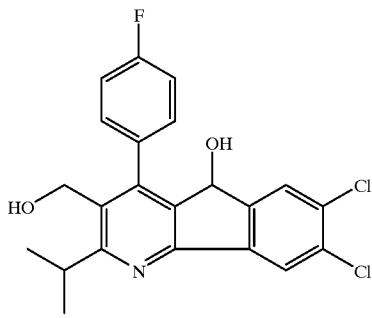

7.4 g of the compound from Example I (16.7 mmol) are dissolved under argon in 155 ml of absolute toluene and 66.6 ml of 1 molar diisobutylaluminium hydride solution in toluene (66.6 mmol) are added dropwise at −70° C. After stirring at −70° C. for 30 min and at −60° C. for 30 min, 15.6 ml of methanol are slowly added dropwise and the cooling bath is removed. The mixture is subsequently diluted with 100 ml of toluene and 900 ml of 20% strength sodium potassium tartrate solution are added and the mixture is stirred for 1 h. After separation of the organic and aqueous phases, the aqueous phase is reextracted with toluene, and the combined organic phases are washed with saturated sodium chloride solution and then dried over sodium sulphate. The crude product concentrated from the organic phase is eluted on 600 g of silica gel (0.04–0.063 mm) using C/EA 8:2.

Yield: 4.47 g (64% of theory)
$R_f$=0.12 (C/EA 8:2)

EXAMPLE III 7,8-Dichloro-4-(fluorophenyl)-2-isopropyl-5-oxo-5H-indeno[1,2-b]pyridine-3-carbaldehyde

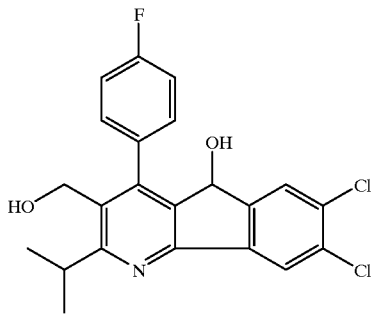

A mixture of 6.8 g of pyridinium chlorochromate (30 mmol) and 3.2 g of alumina (30 mmol) is added at room temperature to a solution of 2.1 g of Example II (5 mmol) in 140 ml of methylene chloride. After 1.5 h, some silica gel is added, the mixture is filtered through 280 g of silica gel and the solid is washed with about 2000 ml of methylene chloride. The combined filtrates are concentrated and dried in a high vacuum.

Yield: 1.8 g (87% of theory)
$R_f$=0.45 (C/EA 8:2)

PREPARATION EXAMPLES

EXAMPLE 1

7,8-Dichloro-4-(4-fluorophenyl)-3-[hydroxy-(4-trifluoromethyl-phenyl)-methyl]-2-isopropyl-indeno[1,2-b]pyridin-5-one

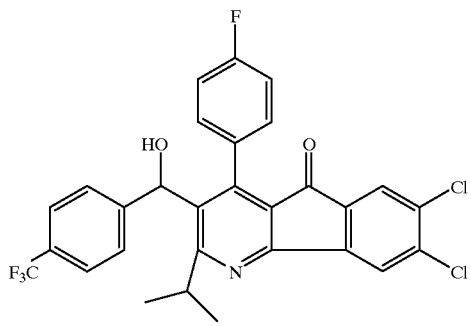

a) Preparation of the Grignard Reagent 100 ml of THF are added under argon to 537 mg of magnesium (22.4 mmol), a few drops of dibromomethane are added and the mixture is heated to reflux. 3.47 g of p-bromobenzotrifluoride (15.6 mmol), dissolved in 20 ml of THF, are slowly added dropwise to the refluxing suspension. After 2 h, it is cooled to room temperature.

b) Grignard Addition to Substance From Example III

The Grignard solution synthesized under a) is added dropwise at −20° C. to a solution of 2.18 g of Example III (5.2 mmol) in 50 ml of THF. After 30 min, 50 ml of saturated ammonium chloride solution are added and the mixture is stirred for 10 min. It is diluted with water and toluene, the phases are separated, the aqueous phase is reextracted with toluene, the combined organic phases are washed with saturated sodium chloride solution and finally the organic phase is dried over sodium sulphate and concentrated. The crude product is eluted on 600 g of silica gel (0.04–0.063 mm) using C/EA 9:1. The eluates are crystallized.

Yield: 2.6 g (89% of theory)
$R_f$=0.32 (C/EA 8:2)

EXAMPLE 2

7,8-Dichloro-4-(4-fluorophenyl)-3-[fluoro-(4-trifluoromethyl-phenyl)-methyl]-2-isopropyl-indeno[1,2-b]pyridin-5-one

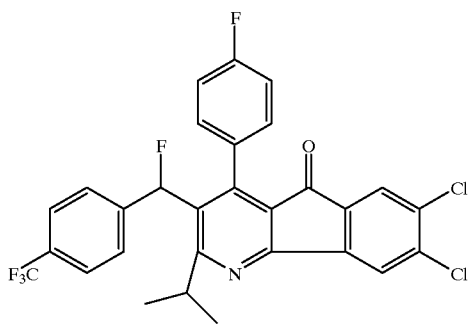

260 mg of Example 1 (0.46 mmol) are dissolved under an argon atmosphere in 10 ml of methylene chloride and 0.06 ml of diethylaminosulphur trifluoride in 1 ml of methylene chloride is added dropwise at −70° C. After 10 min at this temperature, 6 ml of saturated sodium hydrogen carbonate solution are added and the mixture is warmed to room temperature. The phases are separated, and the organic phase is washed again with water, dried over sodium sulphate, filtered and concentrated. It is eluted on 20 g of silica gel (0.04–0.063 mm) using C/EA 95:5.

Yield: 184 mg (71% of theory)

$R_f$=0.43 (C/EA 9:1)

EXAMPLE 3

7,8-Dichloro-4-(4-fluorophenyl)-3-[fluoro-(4-trifluoromethyl-phenyl)-methyl]-2-isopropyl-5H-indeno[1,2-b]pyridin-5-ol

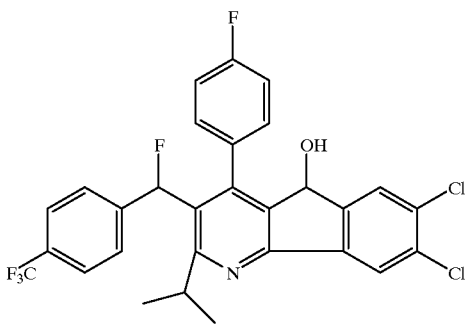

16 mg of sodium borohydride (0.4 mmol) are added at 0° C. to a solution of 122 mg of Example 2 (0.2 mmol) in 10 ml of methanol and the mixture is stirred at room temperature for 2 h. It is treated with saturated ammonium chloride solution and extracted three times with toluene. The combined organic phases are dried over sodium sulphate, filtered and concentrated. The crude product is eluted on silica gel (0.04–0.063 mm) using C/EA 97:3.

Yield: 119 mg (97% of theory)

$R_f$=0.17 (C/EA 9:1)

Separation of the Diastereomers

By means of preparative HPLC (250×25 mm, RP18, 7 μm; flow rate 6 ml/min with acetonitrile/water 8:2).

110 mg of the compound Example VI are separated by means of the column in 2 injections.

Yield: 56 mg of diastereomer A, 41 mg of diastereomer B $R_f$=0.17 (C/EA 9:1)

The compounds shown in Table 1 are prepared in analogy to the procedures of Examples 1–3:

TABLE 1

| Ex.-No. | D | E | R¹⁹/R²⁰ | Isomer | $R_f$ |
|---|---|---|---|---|---|
| 4 | 4-(trifluoromethyl)-α-fluoroethyl-phenyl | isobutyl | H/H | Diasteromer mixture 2:2 | 0.13 C/EA 9:1 |
| 5 | 4-(trifluoromethyl)acetyl-phenyl | isobutyl | H/H | | 0.13 C/EA 9:1 |
| 6 | 4-(trifluoromethyl)-α-fluoroethyl-phenyl | isobutyl | H/H | Diastereomer 1 | 0.13 C/EA 9:1 |
| 7 | 4-(trifluoromethyl)-α-fluoroethyl-phenyl | isobutyl | H/H | Diastereomer 2 | 0.13 C/EA 9:1 |
| 8 | 4-(trifluoromethyl)-ethyl-phenyl | isobutyl | H/H | | 0.18 PE/EA 10:1 |
| 9 | 3-(trifluoromethyl)-α-fluoroethyl-phenyl | isobutyl | H/H | Diastereomer 1 | 0.15 C/EA 9:1 |

TABLE 1-continued

| Ex.-No. | D | E | R¹⁹/R²⁰ | Isomer | $R_f$ |
|---|---|---|---|---|---|
| 10 | 3-CF₃, F-phenyl-CH(CH₃)- | H₃C-CH(CH₃)-CH₂- (isobutyl) | H/H | Diastereomer 2 | 0.14 C/EA 9:1 |
| 11 | 4-CF₃-phenyl-CH(F)(CH₃)- | isobutyl | H/H | Enantiomer I1 | 0.13 C/EA 9:1 |
| 12 | 4-CF₃-phenyl-CH(F)(CH₃)- | isobutyl | H/H | Enantiomer I2 | 0.13 C/EA 9:1 |
| 13 | 4-CF₃-phenyl-CH(F)(CH₃)- | isobutyl | H/H | Enantiomer II1 | 0.13 C/EA 9:1 |
| 14 | 4-CF₃-phenyl-CH(F)(CH₃)- | isobutyl | H/H | Enantiomer II2 | 0.13 C/EA 9:1 |
| 15 | 2-F, 4-CF₃-phenyl-CH(F)(CH₃)- | isobutyl | H/H |  | 0.15 C/EA 9:1 |

TABLE 1-continued

| Ex.-No. | D | E | $R^{19}/R^{20}$ | Isomer | $R_f$ |
|---|---|---|---|---|---|
| 16 | 4-(trifluoromethyl)benzoyl | cyclopentyl | H/H | | 0.18 + 0.28 C/EA 8:2 |
| 17 | 1-[4-(trifluoromethyl)phenyl]-1-fluoroethyl | cyclopentyl | H/H | Diastereomer 1 | 0.12 C/EA 9:1 |
| 18 | 1-[4-(trifluoromethyl)phenyl]-1-fluoroethyl | cyclopentyl | H/H | Diastereomer 2 | 0.12 C/EA 9:1 |
| 19 | 4-(trifluoromethyl)benzoyl | cyclopentyl | H/H | | 0.13 C/EA 9:1 |
| 20 | 4-(trifluoromethyl)benzyl | cyclopentyl | H/H | | 0.18 C/EA 9:1 |
| 21 | 1-[4-(trifluoromethyl)phenyl]-1-fluoroethyl | cyclopentyl | H/H | Enantiomer 4 | 0.12 C/EA 9:1 |

TABLE 1-continued

[Structure: 4-(4-fluorophenyl)-5-hydroxy substituted indeno-pyridine core with D, E, R19, R20 substituents]

| Ex.-No. | D | E | R19/R20 | Isomer | Rf |
|---|---|---|---|---|---|
| 22 | 4-Cl-3-CF3-phenyl-CH(OH)CH3 | OH | cyclopentyl-CH2 | H/H | Diastereomer mixture | 0.13 + 0.21 C/EA 8:2 |
| 23 | 4-Cl-3-CF3-phenyl-CH(OH)CH3 | | cyclopentyl-CH2 | H/H | Diastereomer 2 | 0.13 C/EA 8:2 |
| 24 | 4-Cl-3-CF3-phenyl-C(=O)CH3 | | cyclopentyl-CH2 | H/H | Racemate | 0.10 C/EA 9:1 |
| 25 | 4-Cl-3-CF3-phenyl-CHF-CH3 | | cyclopentyl-CH2 | H/H | Diastereomer mixture | 0.33 C/EA 8:2 |
| 26 | 4-CF3-phenyl-CHF-CH3 | | isobutyl (H3C-CH(CH3)-CH2) | 3-Cl/4-Cl | Diastereomer 1 | 0.17 C/EE 9:1 |
| 27 | 4-CF3-phenyl-CHF-CH3 | | isobutyl (H3C-CH(CH3)-CH2) | 3-Cl/4-Cl | Diastereomer 2 | 0.17 C/EE 9:1 |

The compounds shown in Table 2 are prepared in analogy to the abovementioned procedures:

TABLE 2

| Ex.-No. | Structure | Isomer | R_f-value |
|---|---|---|---|
| 28 | 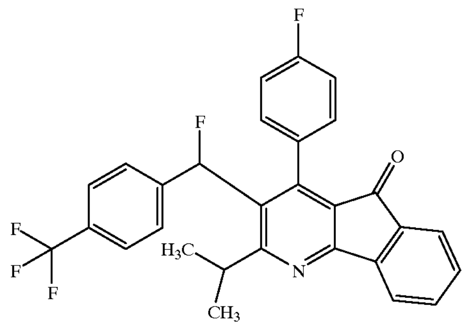 | | 0.38 Cy/CE (9:1) |
| 29 | 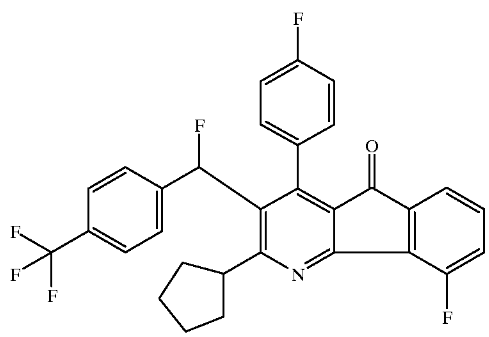 | Racemate-mixture | 0.55 PE/EA (9:1) |
| 30 | 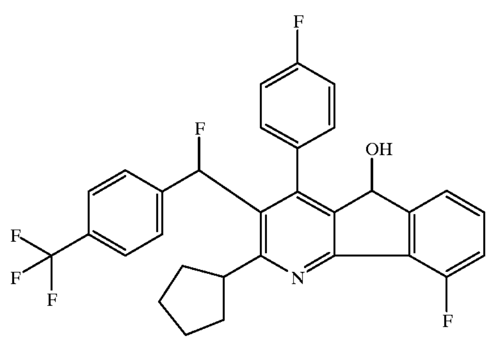 | Diastereomer mixure (1:1) | 0.22 PE/EA (10:1) |
| 31 | 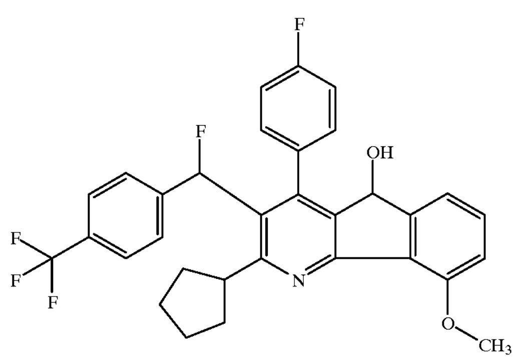 | Diastereomer mixure | 0.24 PE/EA (5:1) |

TABLE 2-continued
| Ex.-No. | Structure | Isomer | $R_f$-value |
|---|---|---|---|
| 32 | 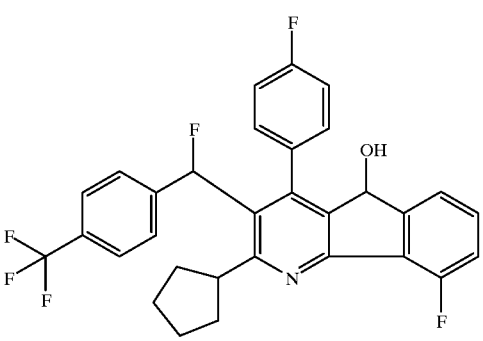 | Diastereomer 1 | 0.22 PE/EA (10:1) |
| 33 | 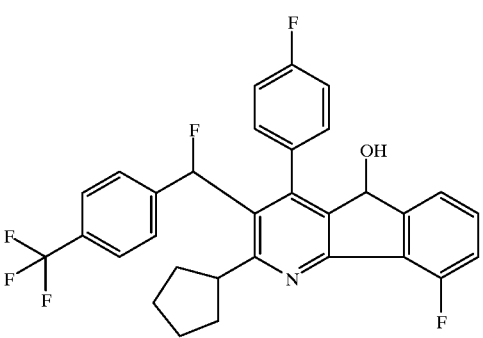 | Diastereomer 2 | 0.22 PE/EA (10:1) |
| 34 | 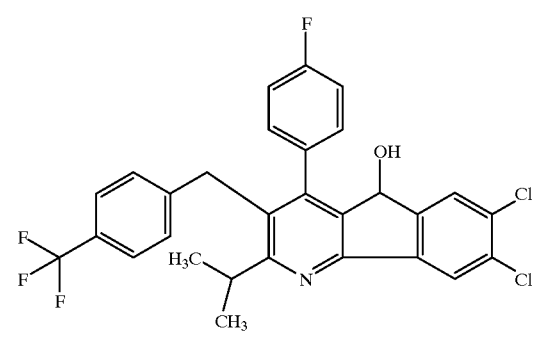 | Racemate | 0.43 Cy/EA (8:2) |
| 35 | 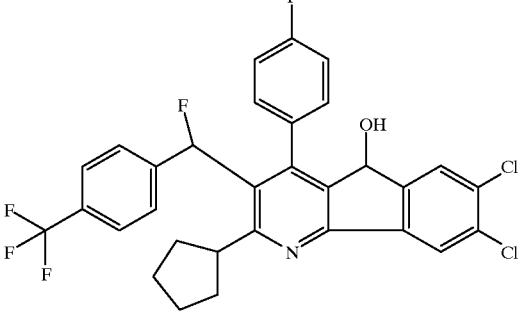 | Diastereomer 1 | 0.30 Cy/EA (9:1) |

TABLE 2-continued

| Ex.-No. | Structure | Isomer | R$_f$-value |
|---|---|---|---|
| 36 | 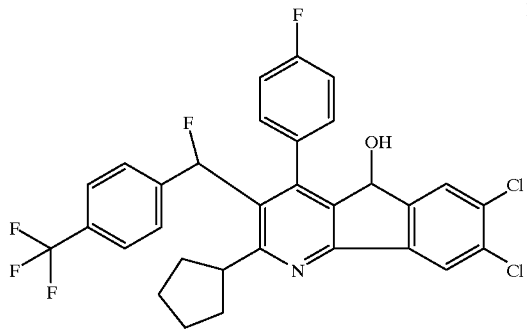 | Diastereomer 2 | 0.30 Cy/EA (9:1) |
| 37 | 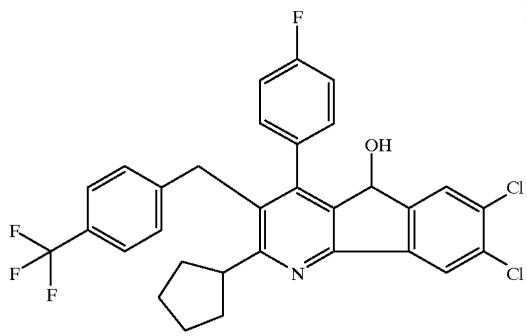 | Racemate | 0.25 Cy/EA (9:1) |
| 38 | 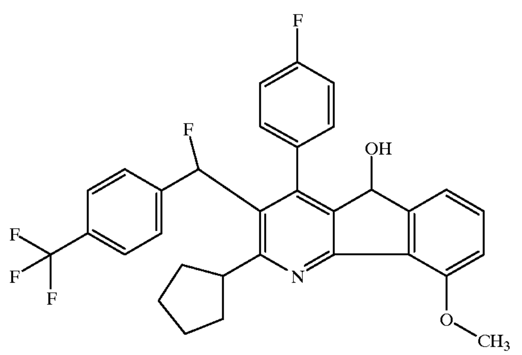 | Diastereomer 1 | 0.24 PE/EA (5:1) |
| 39 | 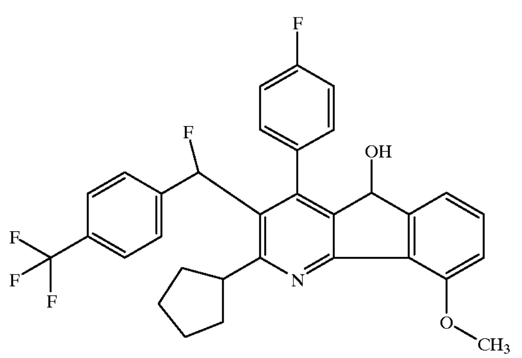 | Diastereomer 2 | 0.24 PE/EA (5:1) |

TABLE 2-continued

| Ex.-No. | Structure | Isomer | $R_f$-value |
|---|---|---|---|
| 40 | 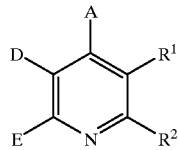 | Enantiomer II 2 | 0.12 Cy/EA (9:1) |

We claim:

1. A bicyclic-fused pyridine of the formula (I):

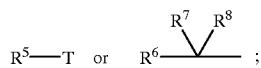

(I)

in which

A represents aryl having 6 to 10 carbon atoms, which is optionally substituted up to 5 times in an identical or different manner by halogen, hydroxyl, trifluoromethyl, trifluoromethoxy, nitro, or by straight-chain or branched alkyl, acyl, hydroxyalkyl or alkoxy each having up to 7 carbon atoms, or by a group of the formula $-NR^3R^4$;

in which $R^3$ and $R^4$ are identical or different and represent hydrogen, phenyl or straight-chain or branched alkyl having up to 6 carbon atoms;

D represents a radical of the formula:

$$R^5-T \quad \text{or} \quad R^6-\overset{R^7\ R^8}{\underset{\phantom{x}}{\vee}}\ ;$$

in which $R^5$ and $R^6$ independently of one another denote cycloalkyl having 3 to 8 carbon atoms, or aryl having 6 to 10 carbon atoms, said cycloalkyl or aryl being optionally substituted up to 5 times in an identical or different manner by trifluoromethyl, trifluoromethoxy, halogen, hydroxyl, carboxyl, nitro, by straight-chain or branched alkyl, acyl, alkoxy or alkoxycarbonyl each having up to 6 carbon atoms, or by phenyl, phenoxy or thiophenyl, which for their part can be substituted by halogen, trifluoromethyl or trifluoromethoxy, or by $-NR^9R^{10}$;

in which $R^9$ and $R^{10}$ are identical or different and have the meaning of $R^3$ and $R^4$ indicated above;

T represents a straight-chain or branched alkylene or alkenylene chain each having up to 10 carbon atoms, and each of which is optionally substituted up to 2 times by hydroxyl;

$R^7$ represents hydrogen or halogen; and $R^8$ represents hydrogen, halogen, azido, trifluoromethyl, hydroxyl, trifluoromethoxy, straight-chain or branched alkoxy having up to 5 carbon atoms, or a radical of the formula $-NR^{11}R^{12}$;

in which $R^{11}$ and $R^{12}$ are identical or different and have the meaning of $R^3$ and $R^4$ indicated above; or $R^7$ and $R^8$, together with the carbon atom to which they are attached, form a carbonyl group;

E represents cycloalkyl having 3 to 8 carbon atoms, or represents straight-chain or branched alkyl having up to 8 carbon atoms, which is optionally substituted by cycloalkyl having 3 to 8 carbon atoms or by hydroxyl;

$R^1$ and $R^2$ together form a straight-chain alkylene chain having 3 carbon atoms, to which a phenyl ring is fused, and is substituted by a group of the formula $-OR^{13}$;

in which $R^{13}$ represents hydrogen;

wherein said fused phenyl ring is optionally substituted up to 3 times in an identical or different manner by halogen, carboxyl or by straight-chain or branched alkyl, alkoxy or alkoxycarbonyl each having up to 6 carbon atoms;

or a salt or a N-oxide thereof.

2. A pharmaceutical composition comprising a compound according to claim 1 and a pharmaceutically acceptable carrier.

3. A method for the treatment of arteriosclerosis, said method comprising administering to a patient in need thereof an effective amount therefor of a compound according to claim 1.

* * * * *